(12) United States Patent
Diaz et al.

(10) Patent No.: US 10,368,548 B2
(45) Date of Patent: Aug. 6, 2019

(54) BIOLOGICAL INOCULANT FOR PROMOTION OF GROWTH IN FOREST SPECIES AND METHOD FOR OBTAINING THE SAME

(71) Applicant: PONTIFICIA UNIVERSIDAD JAVERIANA, Bogota (CO)

(72) Inventors: Lucía Ana Diaz, Bogota (CO); Lina Marcela Morales Palencia, Bogota (CO); Juan Sebastian P. Beltran Acosta, Bogota (CO)

(73) Assignee: PONTIFICIA UNIVERSIDAD JAVERIANA, Bogotá (CO)

( * ) Notice: Subject to any disclaimer, the term of this patent is extended or adjusted under 35 U.S.C. 154(b) by 0 days.

(21) Appl. No.: 14/783,393

(22) PCT Filed: Apr. 10, 2014

(86) PCT No.: PCT/IB2014/000527
§ 371 (c)(1),
(2) Date: Oct. 8, 2015

(87) PCT Pub. No.: WO2014/167409
PCT Pub. Date: Oct. 16, 2014

(65) Prior Publication Data
US 2016/0066583 A1 Mar. 10, 2016

(30) Foreign Application Priority Data
Apr. 11, 2013 (CO) .................................. 13094384

(51) Int. Cl.
| C12N 1/20 | (2006.01) |
| A01N 63/00 | (2006.01) |
| A01N 63/02 | (2006.01) |
| C05B 17/00 | (2006.01) |
| C05F 11/08 | (2006.01) |

(52) U.S. Cl.
CPC ............. *A01N 63/02* (2013.01); *A01N 63/00* (2013.01); *C05B 17/00* (2013.01); *C05F 11/08* (2013.01); *C12N 1/20* (2013.01)

(58) Field of Classification Search
None
See application file for complete search history.

(56) References Cited

FOREIGN PATENT DOCUMENTS

| CN | 1548404 A | 11/2004 |
| CN | 101318852 A | 12/2008 |
| KR | 92-3238 B1 | 4/1992 |
| KR | 96-2627 B1 | 2/1996 |

OTHER PUBLICATIONS

Aeron et al., J. Gen. Appl. Microbiol. (2012), vol. 58, pp. 121-127.*
International Search Report, issued in PCT/IB2014/000527, dated Sep. 3, 2014.

* cited by examiner

*Primary Examiner* — Hasan S Ahmed
*Assistant Examiner* — Frank Choi
(74) *Attorney, Agent, or Firm* — Birch, Stewart, Kolasch & Birch, LLP

(57) ABSTRACT

The invention relates to the production and application of a biological inoculant for use in plant material sown in nurseries. The invention also relates to a method for the immobilization of bacterial strains on a support and application to plant materials. The invention further relates to the use of native teak tree rhizosphere bacteria as a means for promoting plant growth. The invention consists in developing a biological product based on applying rhizosphere bacteria to a carbonized teak sawdust support, which can be used to obtain plants with improved characteristics in less time.

20 Claims, 5 Drawing Sheets

BIOLOGICAL INOCULANT FOR PROMOTION OF GROWTH IN FOREST SPECIES AND METHOD FOR OBTAINING THE SAME

TECHNICAL FIELD

The present invention relates to the field of agricultural biotechnology and the application of biological inoculants for promoting plant growth without affecting the environment.

BACKGROUND OF THE INVENTION

In 2009 the timber industry produced USD $91,898,016,000 in global imports and about USD $89,787,048,000 in exports, indicating it is a sector with high economic impact on the world. In Colombia's case, 2009 saw USD $46 million in wood exports and imports of USD $104.556 million, demonstrating a flaw in timber production to meet domestic demand (TradeMap, 2011).

The main input for wood production are forest species such as oak, pine, eucalyptus, cypress and walnut. The World Bank estimates that some 1.2 billion jobs depend on the forest industry, which is mainly developed in Africa, Latin America and Asia. In Colombia, 70% of the productive forest area consists of introduced species such as araucaria, ash, cypress, various pines, eucalyptus and teak, among others.

Forest plantations of these species are generally located in abandoned and low fertility farmland, which has generated several disadvantages from the initial stages of growth, related to fertilization problems, low percentage of mycorrhization, and a high incidence of disease (Jaramillo & Martinez-Nieto, 2009). All this has led to development and implementation of a variety of products useful in the early growth stages of these species.

In addition, there is currently a high interest for activities involving and use of environmentally sustainable products, such as biofortified substrates and biological inoculants. The latter are understood as products that contain viable beneficial microorganisms used in agriculture for fixing nitrogen, solubilization of nutrient carrier materials, promotion of plant growth, mycorrhizal colonization or transformation of organic matter. These products should not contain microorganisms pathogenic to humans, plants or animals (Pardo, 2002; Soroa et al., 2006; NTC 5842, 2011).

The use of microorganisms in the development of these products is important, as they are the most important soil component and responsible for the dynamics of plant transformation and development. The presence of these microorganisms in soil makes it fertile, that is, increases the concentration of nutrients available to the plant or microbial populations that release nutrients and allow good plant development.

Among the microorganisms, bacteria and arbuscular mycorrhizal fungi have been recognized by the Food and Agriculture Organization-FAO as an important tool to increase agricultural production and provide benefits to plants in protection and obtaining of nutrients (Ocampo et al., 2001). Some characteristics of these microorganisms are that they do not require internal colonization of plant tissues to act; having the ability to increase their population density in the rhizosphere in a short time after inoculation; and effectively colonizing the root surface (Jimenez et al., 2001).

In the specific case of fungi, the most important advantages are evident in the increased capacity to obtain phosphorus and in improvement of water relations and adaptation to soil by plants produced in the nursery (Ocampo et al., 2001). The bacteria in turn promote interaction between plant roots and fungi, bioprotective action, and plant development, and are involved in the production of plant growth regulators such as 3-indole acetic acid (IAA); they also facilitate the assimilation of nitrogen and inorganic salts. Other advantages are associated with increased vigor, emergence and seedling weight and further development in root systems, and an increase of up to 30% in production (Jimenez et al., 2001; Bertolini et al., 2007).

Regarding the species *Pseudomonas* sp. and *Enterobacter* sp., they have been used as bio-fertilizers or growth promoters in *Lactuca sativa* (Kohler, 2009), tomato (Gamalero, 2002, Pivato et al., 2009), in *Medicago truncatula*, in tobacco (Ramamoorthy et al., 2001) and in rice (Nandakumar, 2001), among others.

Regarding *Enterobacter* sp., it was revealed that has been used in promoting growth in canola (Saleh, 2001; Mayak, 2001; Nie et al., 2002), tomato (Holguin, 2003), carnation (Li et al., 2005) and sugar cane (Mirza et al., 2001), among others.

The passage of nutrients, oxygen transfer and adhesion of a microbial population to plants is favored by using microbial media. Using media is important because, when introducing microorganisms to different environments without a support, they can have low survival rates for the first ones and a low efficiency due to the low number of colony forming units per gram of soil. Use of supports allows greater survival in inoculation processes and yet does not cause pollution in the environment in which they are applied. Such microbial supports are also known as microbial carriers.

However, some limitations arise when using certain media. For example, when peat is used as a support, in addition to its high cost and low availability in our tropical countries, we note the low purity in the support, since after 90 days of cold storage inoculants begin to show contamination with various microorganisms other than those immobilized (Stephens & Rask, 2000), such as Gram-positive bacilli. With bamboo sawdust, cell viability is not maintained, and in the case of a sodium alginate support, although the purity, viability and biological activity are maintained, the costs of obtaining the inoculant are high.

Within the supports used for this purpose, the prior art discloses different types, according to the compounds of porous materials such as polyurethane, cellulose, polypropylene and ceramics. These supports are characterized because they allow immobilizing cells of animals, plants, microorganisms and protozoa. Cellulose supports are susceptible to erosion, therefore their duration is shorter, and ceramic supports have several limitations due to their high specific gravity which prevents them from being fluid in water.

Another type of supports is composed of gels, including compounds for polyacrylamide, polyethylene glycol and alginic acid. The gel supports may contain large quantities of water, so they have greater biocompatibility with microorganism, human and plant cells.

For promotion of plant growth and the agriculture industry, the most commonly used supports are clay, vermiculite, perlite, sepiolite, kaolin, diatomaceous earth, and natural zeolite, among others, as shown in patent application WO2009/027544A1.

Other inventions relating to the use of supports, where sawdust is used, have been identified in the prior art, such as Patent Document JP2000016889 that relates to a process for the production of manure as a fermentation fertilizer using photosynthetic bacteria of the genera *Rhodopseudomonas*, *Rhodospirillum* and *Ectothiorhodospira*, and the families Ectothiorhodospiraceae and Chloroflexaceae, with acetic acid or a material containing it, and in which the mixture on a porous material (30% w/w or less) is used as adsorbent produced by carbonization of wood, sawdust, coconut shells, bagasse, wheat hulls, cottonseed hulls, coffee grounds or the like, a zeolite, etc.

Importantly, this document merely discloses the requirement of a 30% (w/w) or less microbial culture with respect to the porous material. Also, this formulation includes a requirement of acetic acid or a source thereof in a ratio of up to eight times the volume of the culture. However, it does not establish a level of particular microorganisms per gram, thus preventing precision dosing of the product's components.

Patent KR960002627 reveals a composting promoter obtained by mixing a uniform part of bacteria with sawdust, rice husks and limestone in proportions (w/w) 4:5:1.

Patent KR920003238 discloses an agent for soil improvement obtained by mixing 94-97% (w/w) of organic waste matter, 2-5% (w/w) of sawdust, 0.2-0.5% of whitewash and 0.2-0.5% ash wood and adjusting the pH to a value between 6.5 and 7.5.

Patent JP11029384 reports an organic fertilizer that promotes plant growth, effectively improves soil quality and allows the reuse of industrial waste. This fertilizer is obtained by mixing rice bran, sawdust from a foliage tree or wood, liquid soy sediments, cut rice plant straw, waste garbage or granular charcoal, with a material comprising a bacterial debris from mushroom cultivation (e.g. Shiitake, Maitake and Shimeji) and fermenting the resulting material.

Patent JP4122788 refers to a soil activator and plant growth promoter obtained by aerobic fermentation of a vegetable source rich in fibers mixed with bran cereal, shellfish fossils, among others, and an enzyme complex, which is mixed with sawdust or enzymatically treated wood chips.

Patents KR960002627 and JP11029384 report separate stages, as in the case of preparing the support (heating and carbonization) and stages of inoculation and incubation, respectively.

According to the above information, there clearly still remains a need for biological inoculants for nursery substrates in order to promote plant growth without affecting the environment and allowing plants to achieve best features of vigor and health in less time, through a process that includes stages of preparing the support, inoculation and incubation, and allowing reduced use of chemical fertilizers.

OBJECT OF THE INVENTION

An object of the invention is a biological inoculant that stimulates plant growth comprising a support derived from an industrial transformation process for teak, and one or more bacterial strains that promote plant growth, preferably bacterial strains isolated from teak roots. This biological inoculant can be combined with suitable excipients to form a product to be applied to plant material prior to planting.

Another object of the present invention is to provide a process for immobilizing carrier strains on a support characterized by the culture time, performing a secondary culture, the storage form of the inoculant, and its application to plant material from clonal propagation by cuttings, pseudo-cuttings or mini-cuttings or from seed-seedling.

Still another object of the invention is a product characterized by comprising the biological inoculant with excipients suitable for the stimulation of plant growth when the product is applied on seeds, seedlings, cuttings, pseudo-cuttings or mini-cuttings.

DETAILED DESCRIPTION OF THE INVENTION

Figure 1:
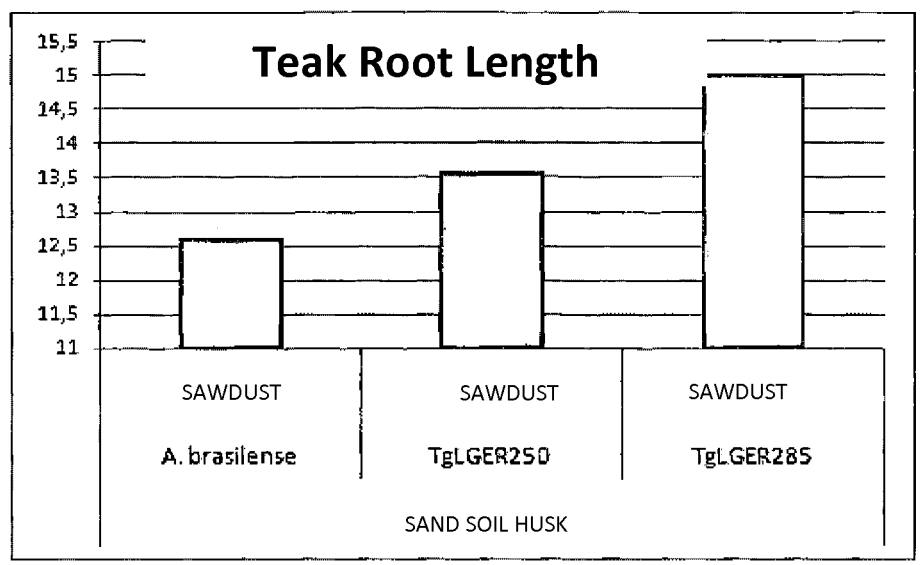
FIG. 1 shows the results in the root length of teak plants inoculated with different bacteria immobilized on the teak sawdust support. The plants were planted in a mixture of sand quartzite, nursery soil and rice husk in a 1:1:1 ratio. The root length was determined 30 days after sowing.

The immobilization process to obtain a biological inoculant that stimulates plant growth of the present invention includes the following steps:

1. Forming a carrier from teak wood sawdust in a size between 400-1000 µm, subjected to a heat treatment so that the sawdust burns evenly, does not generate ash, possesses a bulk density of 0.1 g/0.2 g/l, preferably 0.167 g/l, its color is between the 7.5R2/4 and 10YR2/4 categories with particles present in 10Y1/2 color according to the Munsell color chart and having the following composition
   i. Total organic carbon from 20% to 40%
   ii. Total nitrogen between 0.1% and 0.5%
   iii. C/N>90
   iv. Cation exchange capacity>20 meq/100 g
   v. Calcium between 8 and 15 meq/100 g
   vi. Magnesium 6 to 12 meq/100 g
   vii. Potassium 4 to 8 meq/100 g
   viii. Sodium 1 to 5 meq/100 g
   ix. Available phosphorus between 400 and 750 ppm 2. Culturing one or more plant growth promoting strains of the negative Gram group of bacteria in a fermentation system until the end of their exponential or logarithmic phase, when they reach maximum cell biomass production and generate secondary metabolites of agroindustrial interest, such as acids and compounds regulating plant growth, removing the supernatant and re-suspending it in 0.85% concentration saline to a final cell concentration of $10^{12}$ CFU/mL.

3. Mixing each solution resulting from step b) with the teak sawdust support obtained in step a) in proportion of inoculum:support from 2:5 to 2:7.

4. Cultivating the mixture obtained in the step for a period of time between 24 and 72 hours at a temperature between 25° C. and 42° C. and optionally including excipients, to obtain the biological inoculant.

The advantages of the invention will be better explained below by obtaining a biological inoculant comprising:

a. A culture of the strain TgLGBR285 of the genus *Stenotrophomonas* deposited in the collection of the Department of Biology at the Pontificia Universidad Javeriana with the number No BIO-PUJ-146, the collection of the Department of Microbiology number CM-PUJ-148, which in turn is registered in the World Federation for Culture Collections (WFCC) with the number 857-CM-DM-PUJ;

b. or a culture of the strain TgLGBR250 of the genus *Enterobacter* deposited in the collection of the Department of Biology at the Pontificia Universidad Javeriana with the number No BIO-PUJ-146, the collection of the Department of Microbiology number CM-PUJ-148, which in turn is registered in the World Federation for Culture Collections (WFCC) with the number 857-CM-DM-PUJ;

c. a teak sawdust support made from hardwood teak that does not require immunization before obtaining the sawdust.

Determining the supports or carriers is one of the critical stages in the product's formulation, because these have to maintain the microorganisms active and viable in a concentration greater than $10^6$ (preferably between $10^6$ and $10^9$ CFU/mL).

Among the characteristics that a support must have to be used in the formulation of microbial bioinoculants are water retention capacity, porosity, absence of toxic and volatile compounds that affect microbial growth, and easy sterilization and handling due to the homogeneity of the particles.

Two of the categories used as supports in the inoculants industry are coal—alone or with mixtures with other materials—and lignin cellulolytic materials including bagasse, husks and sawdust (D'Souza and Godbole, 2002; Pandey and Maheswari, 2007). The sawdust contains macropore structures such as labyrinthines, which provide a large binding surface area for bacteria (Podorozhko et al., 2008).

Kostov and Lynch (1998) used composted sawdust as support for inoculants based on Gram negative nitrogen-fixing bacteria of the genera *Rhizobium, Bradyrhizobium* and *Azospirillum* with good results on growth of plants and inoculated microorganisms. However the composting process is slow (it takes more than 40 days) and the effect on growth can be masked by materials that are added in the composting process. On the other hand De Brito-Alvarez (1995) used as a support for bacteria a mix of compost, sawdust, rice husks and bagasse, but tomato plants exhibited phytotoxicity. In other studies with sawdust as support, an initial decline was reported for populations of Gram negative bacteria as *Bulkholderia* sp. from $10^9$ CFU/g to $10^7$ CFU/g (Maheshwari and Pandey, 2007).

No reports were found on the use of teak sawdust as a support in formulating bioinoculants. One reason is related to its antimicrobial effect. The natural durability of Teak wood is high, being resistant to degradation of chromogenic fungi and rot (Peraza, 2002). This durability in its heartwood, the main constituent of sawdust, has been ascribed to the proportion of tectoquinone and naphthoquinone, aromatic compounds from the anthroquinone group (Thulasidas and Bhat, 2007), used as antimicrobial compounds with non-generalized effect. Although no negative effects are reported for other plant species on their anthraquinone Gram negative bacteria such as *Pseudomonas* sp. (Chukwujekwu et al., 2006), for teak extracts there are studies of its detrimental effect on some genera of this bacterial group (Thulasidas and Bhat, 2007; Krishna & Jayakumaran, 2010).

Unburned teak sawdust has a total oxidizable organic carbon content between 46 and 48%, silica between 1.5% and 2%, organic nitrogen between 0.35 and 0.38%, high lignin content between 46 and 56%, cellulose between 30 and 40%, hemicellulose between 7 and 12%, and a carbon:nitrogen ratio between 125 and 131. The latter is less than that reported for other sawdust, C:N=300 (Pandey and Maheshwari, 2007).

The biological inoculant support derived from the process of industrial teak transformation according to the invention can be sawdust from industrial teak wood processing and may have a particle size between 400 to 1000 microns.

The support derived from the process of industrial teak transformation according to the invention is obtained by controlled combustion and sterilization of the material and said support has the following characteristics and composition:

Total organic carbon from 20% to 40%
Total nitrogen between 0.1% and 0.5%
C/N>90
Cation exchange capacity>20 meq/100 g
Calcium between 8 and 15 meq/100 g
Magnesium 6 to 12 meq/100 g
Potassium 4 to 8 meq/100 g
Sodium 1 to 5 meq/100 g
Phosphorus available between 400 and 750 ppm We note that these physicochemical values exhibited by the sawdust are within the recommended ranges for various organic and inorganic media, as reported by authors like Pandey and Maheshwari in 2007 (Pandey, P Y MAHESHWARI, D K 2007. Bioformulation of *Burkholderia* sp. MSSP with a multispecies consortium for growth promotion of Cajanus cajan. Canadian Journal of Microbiology 53: 213-222).

Sawdust can also be obtained by a combustion process, for example in a Neycraft JFF2000® muffle. Fresh sawdust with moisture content between 50% and 60% is placed on a tray forming a layer of preferably 1.5 cm thick, and placed in the flask preheated to 250° C. After 60 minutes in the muffle, it is temporarily withdrawn for a first homogenization process. The material is then fed back into the flask and left for an additional 30 minutes. At the end of this time, the material is removed from the flask and a second homogenization process is performed to prevent the top layer from calcination.

This sawdust obtained from the combustion process is moistened with saline and autoclaved at 121° C. and 0.72 KPa (15 psi) in three cycles, each lasting between 50 minutes and 100 minutes, with a rest period for the material of 20 to 25 hours between each cycle. The product obtained is a burned and sterilized teak sawdust support.

The TgLGBR250 the bacterial strain is characterized as a short Gram-negative *bacillus*; its most important biological activity is to solubilize phosphorus, relative to the reference strain, *Pseudomonas fluorescens* ATCC BAA 477, solubilizing said element to a greater extent and reaching 8 mm halos in Pikovskaya agar and indole derivative concentrations of 75.73 mg/L in nutrient broth supplemented with tryptophan 0.2% (w/v).

Furthermore, the bacterial TgLGBR285 strain is characterized as a short Gram negative *bacillus*, producing indole derivatives in concentrations of 195.83 mg/L in culture in nutrient broth supplemented with 0.2% tryptophan (w/v), comparable with the reference strain ATCC 29145 *Azospirillum brasilense*, which produces 247 mg/L.

The isolation method for TgLGBR285 and TgLGBR250 strains from teak root is performed on the King B® culture medium; solubilization of phosphorus is evaluated in Picovskaya medium (Pikovskaya, 1948); and production of indoleacetic acid is evaluated nutrient broth supplemented with tryptophan 0.2% (w/v).

The immobilization process starts with a batch fermentation culture in Difco® nutrient broth of the bacterial strain isolates. The TgLGBR285 strain is cultured for a period of 8 to 24 hours, where it achieves concentrations over 109 CFU/mL, and the TgLGBR250 strain is cultured for a period of 3 to 15 hours and reaches concentrations exceeding 109 CFU/mL.

This procedure is performed in a batch fermentation system, for example on a scale bioreactor with an effective working volume of 1 liter, at a stirring speed between 110 rpm and 150 rpm and a temperature between 28° C. and 35° C.

It is then centrifuged at 4500 rpm for 15 minutes and the cell precipitate is re-suspended in 1 L of saline. The centrifugation process is repeated and washed twice. The precipitate from the final centrifugation is re-suspended in saline 8.5 g/L by adjusting a concentration of 1012 CFU/mL for each of the two strains.

The resulting inoculum for each strain was mixed with the burned and sterilized teak sawdust carrier. Prior to the completion of mixing, the sawdust support is moistened with saline concentration at 8.5 g/l (ratio 0.5:5 ml/g and 2.5:5 ml/g) and then mixed with the inoculum resulting from each strain in a proportion of 3 to 5 ml inoculum per 5 to 7 g sawdust support.

The mixture is allowed to culture for a period of between 24 and 72 hours at a temperature between 29° C. and 35° C., which is known as a secondary culture. The product obtained at the end of this secondary culture is the biological inoculant comprising a teak sawdust support and one or more bacterial strains that promote plant growth. Bacteria included in this patent document are mesophilic and therefore their growth temperature is between 25° C. and 42° C., with an optimum between 28 and 32° C.

The biological inoculant maintains its viability and biological activity up to 120 days at a concentration above $10^{10}$ CFU/mL in the case of the TgLGBR285 strain and more than $10^{11}$ CFU/mL in the case of the TgLGBR250 strain. Both values are comparable with those of the control strain ATCC 29145 Azospirillum brasilense which achieved a concentration of $10 \times 10^{11}$ CFU/g. Also, 100% purity is achieved under these conditions.

A pasty product can be prepared with the biological inoculant obtained, by mixing 720 mL of carboxymethylcellulose having a concentration of 4 g/L previously autoclaved and 180 g of biological inoculant. The mixture obtained is applied on plant material allowing a contact time between the mixture and the plant material of at least 15 minutes before planting without the material becoming dehydrated. Inoculum concentration at the time of application of the mixture on the plant material is greater than or equal to $10^{11}$ CFU/g inoculant biological+carboxymethylcellulose mixture, fulfilling the minimum limit ($10^7$ CFU/g). The pasty product obtained has a final volume of 900 ml whose performance is: 2200 mini-cuttings or 1220 cuttings or 459 inoculated seedlings. The ratio of inoculant grams and carboxymethylcellulose solution is 4:20, i.e. 4 grams of inoculum per 20 mL of carboxymethylcellulose.

The immobilization process of the strains for the stimulating biological inoculant can be condensed in the following steps according to the above indications:

a. Culturing the TgLGBR285 strain for a period of 8 to 24 hours in a batch fermentation system at a stirring speed between 110 rpm and 150 rpm and a temperature between 28° C. and 35° C.;

b. Culturing the TgLGBR250 strain for a period of 3 to 15 hours in a batch fermentation system at a stirring speed between 110 rpm and 150 rpm and a temperature between 28° C. and 35° C.;

c. separately centrifuging the product of step b to 4,500 rpm for 15 minutes and removing the supernatant;

d. re-suspending the cell precipitate of each strain in saline concentration between 1 to 20 g/L;

e. repeating steps c and d twice;

f. mixing the teak sawdust support with the resulting inoculum for each strain at a ratio between 2 and 3 ml inoculum per 5 to 7 g sawdust support.

g. performing a secondary culture for the mixture for a period between 24 and 72 hours at a temperature between 25° C. and 42° C.

Moreover, in a preferred embodiment of the invention, the process of immobilization of one or more bacterial strains that promote plant growth to obtain the biological inoculant stimulator according to the invention is characterized in that the process comprises the steps of:

a. culturing each strain to be employed in a batch fermentation system for a period of 8 to 24 hours with stirring between 110 and 150 rpm and a temperature between 28° C. and 35° C.;

b. centrifuging the product of step a and removing the supernatant;

c. re-suspended in saline solution of less than 20 g/L concentration for each strain of precipitate obtained in the step;

d. repeating the steps twice for each strain to be used;

e. mixing each solution resulting from the step with the teak sawdust support interval at a ratio of inoculum:support from 2:5 to 2:7;

f. culturing the mixture obtained in the step for a period of time between 24 and 72 hours at a temperature between 25° C. and 42° C.

We note that the stated ratio is adjusted to the water retention capacity of the supports cited by Pandey and Maheshwari in 2007, and maintains the bacterial concentration of $10^{11}$ CFU/g of support.

In a preferred embodiment of the invention, the burnt sawdust support is moistened with a sodium chloride solution (NaCl) of 8.5 g/L at 0.5 to 2.5 milliliters of solution per 5 grams of carrier.

EXAMPLES

The following examples illustrate the scope of the invention:

The biological inoculant in its two formulations with the TgLGBR285 strain and the other TgLGBR250 formulation were compared with the phytohormone AIB (indole butyric acid) and with the ATCC 29145 Azospirillum brasilense strain, which is used in a known commercial formulation.

Example 1

This test was conducted to assess the length of the teak plant roots. In this example the following strains were compared: TgLGBR285+teak sawdust support, TgLGBR250+teak sawdust support, and Azospirillum brasilense+teak sawdust support, in different types of planting substrate in a nursery. This assay was performed with teak mini-cuttings and root length was determined 30 days after sowing, where the *Azospirillum brasilense* strain was used as control.

In this sense, the results presented in FIG. 1 showed that TgLGBR285+teak sawdust support and TgLGBR250+teak sawdust support, were better than the reference and commercial strain *Azospirillum brasilense*+teak sawdust support in the Teak growth variable evaluated: root length. In the first case, a length of 15.02 cm was obtained; in the second a length of 13.59 cm and was obtained, and for *Azospirillum* sp. 12.61 cm in length was found, as shown in FIG. 1.

In this same sense, the inoculant effect was evaluated using two supports or carriers on the length of the root of teak plants planted in peat for 50 days, by using plant growth promoting microorganisms and a plant hormone.

Figure 2:
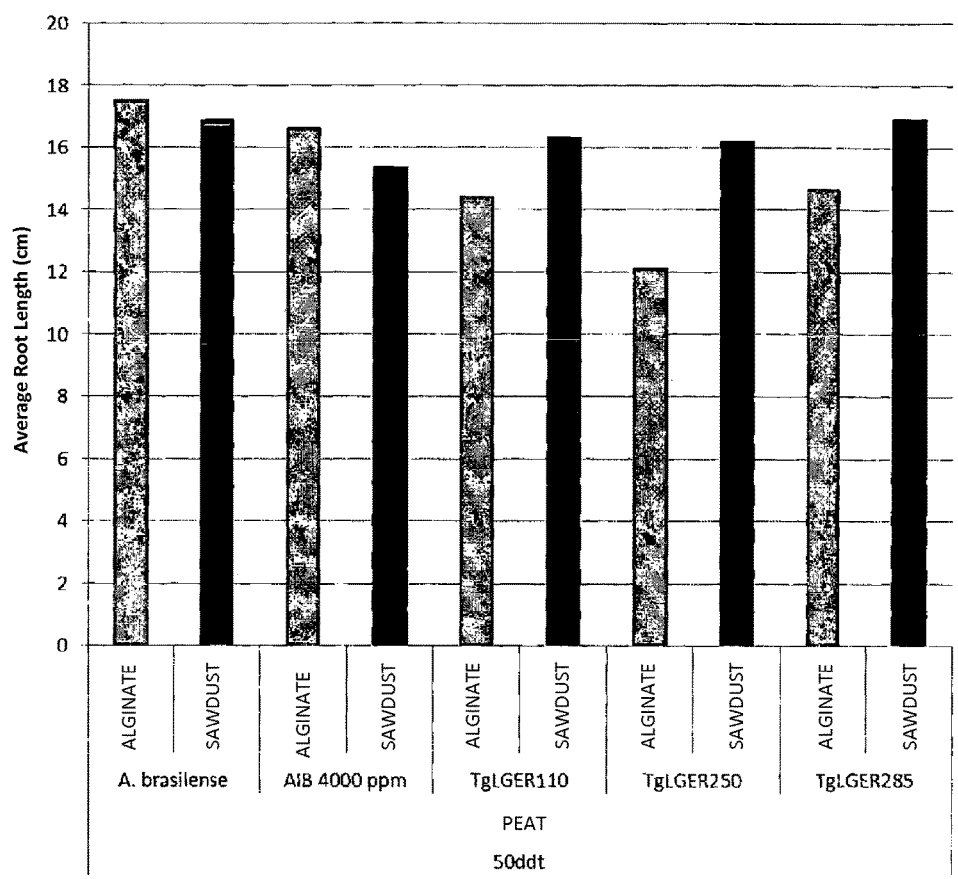
FIG. 2 shows the effect of the biological inoculant using two supports (alginate and teak sawdust) or carriers on the root length of teak plants planted in peat for 50 days, using various plant growth promoting microorganisms and a commercial phytohormone.

In assessing the root length of planted teak plants, the data in FIG. 2 shows a better result by using teak sawdust as a carrier for immobilizing the TgLGBR110, TgLGBR285 and TgLGBR250 microorganisms obtained from teak roots, compared to the use of sodium alginate as a support used in the prior art. In the period of 50 days from sowing to using as an evaluation variable the length of root plants, it is observed that the results obtained with the reference strain and chemical fertilizer are equivalent to the teak sawdust support and alginate, which is consistent with that observed in Example 5, and shows that the biological inoculant of the invention allow superior results without using chemicals and superior to those obtained with the reference strain used in the prior art fertilizers.

Figure 3:
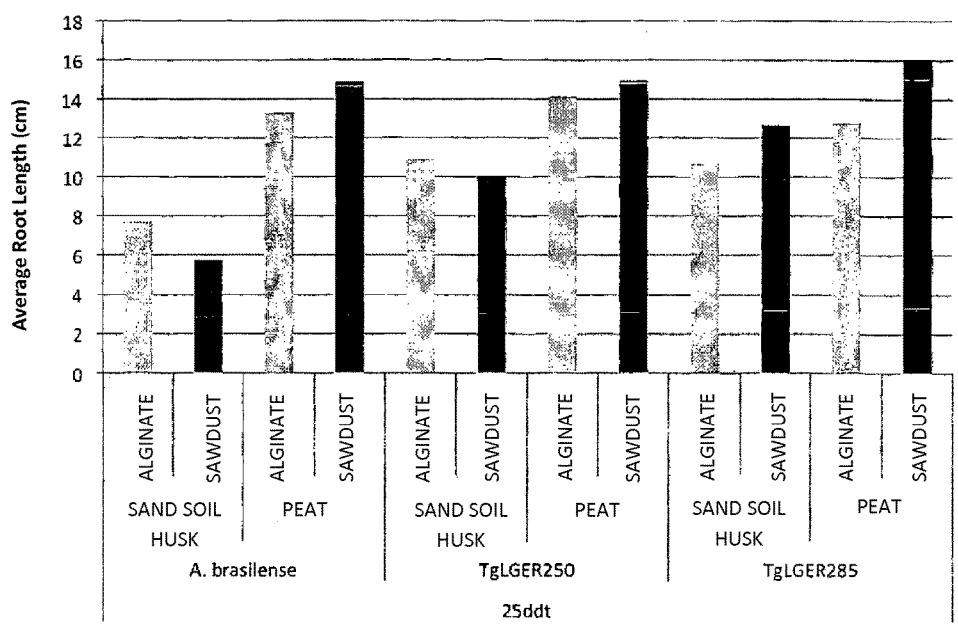
FIG. 3 shows the effect of the biological inoculant using two supports or carriers on the length of teak plant roots, planted for 25 days, using various plant growth promoting microorganisms and different substrates for planting: peat and mixture of sand, soil and husk.

FIG. 3 shows the effect of inoculant using two supports or carriers on the length of the root in teak plants planted for 25 days using two different substrates. Thus, the effect of using biological inoculant in root length was evaluated. For this evaluation, biological inoculants were obtained using the TgLGBR285, TgLGBR250 and *Azospirillum brasilense* strains (strain control) and the immobilization process described herein using both supports: the teak sawdust and sodium alginate supports.

The results reported in FIG. 3 show a superior or equivalent plant growth in the two planting substrates evaluated, using the biological inoculant with the teak sawdust support according to the invention, and sodium alginate used as a support in conventional manner. The length of the root is higher when using the biological inoculant with teak sawdust support versus that employing alginate, inoculated with the TgLGBR285 strain in the two substrates tested. By planting in peat using the biological inoculant with teak sawdust as support, the results are generally higher.

Example 2

Figure 4:
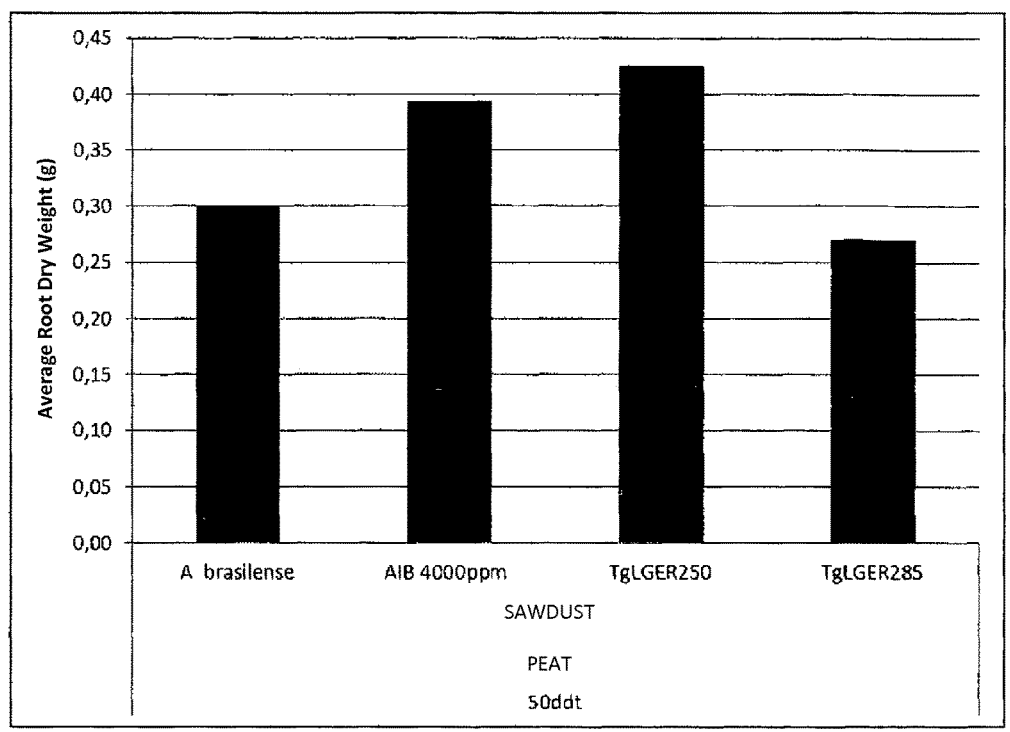
FIG. 4 shows the effect on biomass obtained after 50 days of culture using a commercial phytohormone and different microorganisms that promote plant growth, immobilized in teak sawdust and sown on peat as a substrate.
Figure 5:
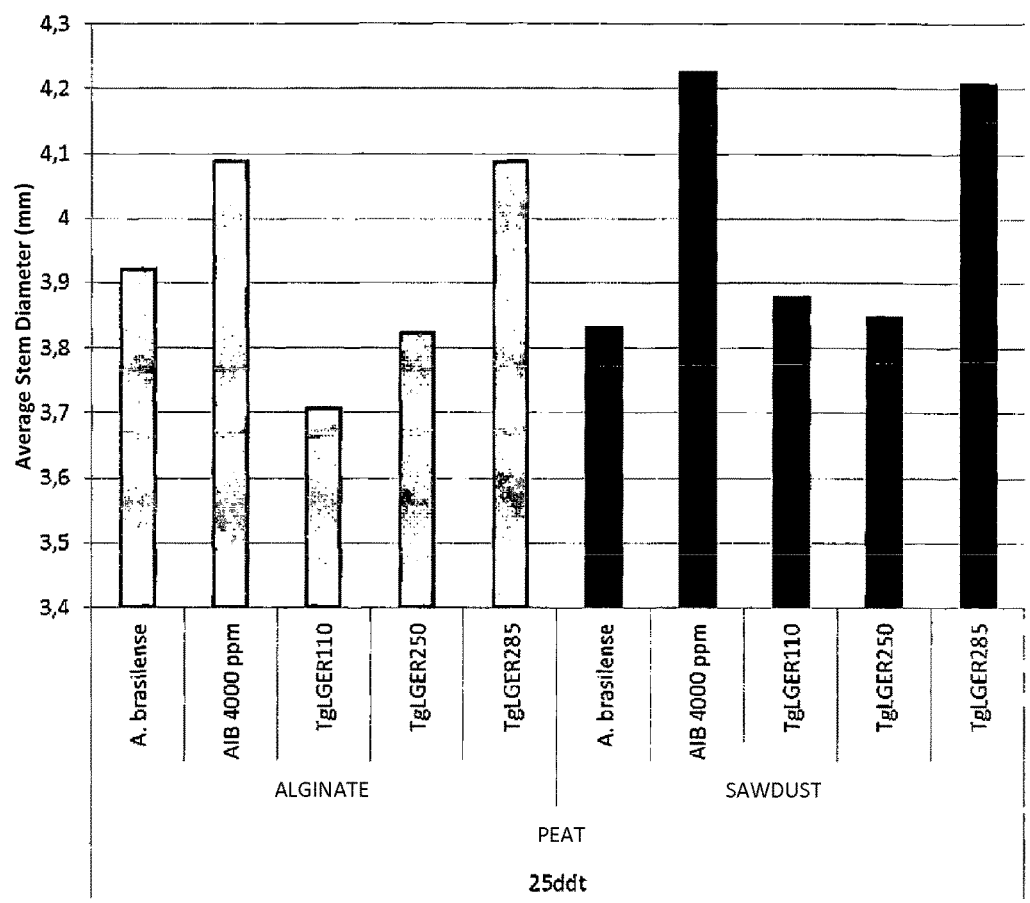
FIG. 5 shows the effect of the biological inoculant on stem diameter in teak plants planted in peat for 25 days, using various plant growth promoting microorganisms and two different supports for immobilization: sodium alginate and teak sawdust.

A trial was performed mini-cuttings from a clonal mini-garden for measuring root biomass for teak plants produced on the nursery floor. In this trial, the comparison was made with the strains TgLGBR285+teak sawdust support, teak sawdust support+TgLGBR250, *A. Brasilense*+teak sawdust, and AIB 4000 ppm plant hormone+teak sawdust over a period of 50 days. All plants were planted in peat. A better result was identified for the root biomass of plants inoculated with the bacteria TgLGBR250 (0.43 g) above the positive control plants to which commercial phytohormone (0.39 g) was applied. The results are shown in FIG. 4. Moreover, the diameter of the plants is substantially higher when using the phytohormone and the three strains evaluated immobilized in the teak sawdust support compared with the results of those immobilized in alginate, which evidence supports the notion that teak sawdust improves the effect of these strains, particularly strain TgLGBR285, obtaining results similar to those obtained with the phytohormone, but without the effects of using a chemical product. Confirming the above, FIG. 5 shows that for the control strain comparable results are obtained between the teak sawdust and alginate, which proves that the teak sawdust support according to the invention is favorable and convenient compared to conventionally known supports in the art.

Example 3

Tests were performed to verify the property of teak sawdust support according to the invention against one of the supports or carriers widely reported in the formulation of plant growth promoting bacteria: sodium alginate.

In this example the viability and stability of the biological activity until day 120 were evaluated after immobilization of different bacteria isolated from teak. The inoculated media were kept at 19±2° C. The biological activity evaluated corresponds to the activity of nitrogenase enzyme present in these nitrogen-fixing bacteria.

The results are presented in Table 1 below. In all cases secondary cultures were performed.

TABLE 1

| Bacterial strain | | Sodium Alginate Support | | Burnt Teak Sawdust Support | |
|---|---|---|---|---|---|
| | | Day 0 | Day 120 | Day 0 | Day 120 |
| TgLGBDR018 | Viability (UFC/g) | $5.7 \times 10^{12}$ | $2.4 \times 10^{11}$ | $5.5 \times 10^{12}$ | $2.1 \times 10^{11}$ |
| | Biological Activity (nmol ethylene/bottle/hour) | 0.43 | 5.82 | 0.62 | 1.06 |
| TgLGBDH238 | Viability (UFC/g) | $5.8 \times 10^{12}$ | $1.6 \times 10^{11}$ | $6.0 \times 10^{12}$ | $8 \times 10^{11}$ |
| | Biological Activity (nmol ethylene/bottle/hour) | 3.6 | 0.97 | 3.05 | 1.31 |
| TgLGBDS203 | Viability (UFC/g) | $6.1 \times 10^{12}$ | $4.9 \times 10^{11}$ | $5.6 \times 10^{12}$ | $1.0 \times 10^{11}$ |
| | Biological Activity (nmol ethylene/bottle/hour) | 1.02 | 0.97 | 0.85 | 0.94 |

In this sense, it can be seen that bacteria immobilized on sawdust teak and stored up to 120 days at room temperature (19±2° C.) maintain their viability and biological activity in similar ranges to those immobilized in sodium alginate, a carrier commonly used in the formulation of biological inoculants. The feasibility reached higher values than those established for biological inoculants according to Colombian Technical Standard NTC 5842 (107 UFC/g).

Example 4

In Example 4, tests were conducted to assess the viability of bacteria isolated from teak and the reference strain ATCC 29145 *Azospirillum brasilense* immobilized in burnt teak sawdust and sodium alginate, stored at 4° C. for 120 days. The results are presented in Table 2 below.

TABLE 2

Table 2

| STRAIN | Burnt Teak Sawdust CFU/g | Sodium Alginate CFU/g |
|---|---|---|
| TgLGBDR110 | $3 \times 10^{12}$ | $3 \times 10^{12}$ |
| TgLGBR248 | $2 \times 10^{12}$ | $1 \times 10^{12}$ |
| TgLGBR250 | $3 \times 10^{12}$ | $7 \times 10^{13}$ |
| TgLGBR285. | $7 \times 10^{11}$ | $3 \times 10^{12}$ |
| *Azospirillum brasilense* | $1 \times 10^{12}$ | $6 \times 10^{11}$ |

As can be seen from the above table, burnt teak sawdust maintains the viability of different teak isolates in values higher than the mentioned technical standard, and also maintains the viability of bacteria isolated from other plant species, such as the *A. brasilense* strain.

Example 5

The following example shows the results of viability of bacteria isolated from *Guadua angustifolia-guadua*, immobilized on burnt teak sawdust and sodium alginate. The assessment was conducted after storing 30 and 45 days, respectively, at 19±2° C. In Table 3 it is evident that again the burnt sawdust teak maintains the viability of the bacteria immobilized on it.

TABLE 3

| STRAIN | Burnt Teak Sawdust CFU/g | Sodim Alginate CFU/g |
|---|---|---|
| GaYaS0038 | $3 \times 10^8$ | $5 \times 10^9$ |
| GaYaR3308 | $2 \times 10^7$ | $1.6 \times 10^8$ |

Finally the feasibility of a bacterium isolated from teak (TgLGBR250) and one isolated from bamboo (GaYaR3308) were evaluated in another organic support, burnt rice husks. For both strains viability was maintained when immobilizing them in burnt teak sawdust, but not when immobilized on the husks. The inoculated media were maintained at 19±2° C. for 2 days. The results of this example are presented in Table 4.

TABLE 4

| STRAIN | Burnt Teak Sawdust CFU/g | Burnt Rice Husks CFU/g |
|---|---|---|
| GaYaR3308 | $10^8$ | <10 |
| TgLGBR250 | $2 \times 10^9$ | <10 |

The invention claimed is:

1. An immobilizing process for obtaining a biological inoculant that stimulates plant growth characterized in that it comprises the steps of:
    a) forming a support medium from teak wood sawdust at a size between 400-1000 μm subjected to a heat treatment such that the sawdust burns homogeneously, does not generate ash, possesses a bulk density of 0.1 g/l to 0.2 g/l, where its color is between the 7.5R2/4 and 10YR2/4 categories with particles present in 10Y1/2 color according to the Munsell color chart and having the following composition:
        i) total organic carbon from 20% to 40%,
        ii) total nitrogen between 0.1% and 0.5%,
        iii) carbon/nitrogen >90,
        iv) cation exchange capacity >20 meq/100 g,
        v) calcium between 8 and 15 meq/100 g,
        vi) magnesium 6 to 12 meq/100 g,
        vii) potassium 4 to 8 meq/100 g,
        viii) sodium 1 to 5 meq/100 g,
        ix) available phosphorus between 400 and 750 ppm;
    b) culturing one or more plant growth promoting strains of the negative Gram group of bacteria in a fermentation system until the end of their exponential or logarithmic phase, when they reach maximum cell biomass production and generate secondary metabolites that increase the solubilization of nutrients in the substrates for sowing plants and increase the plant growth, wherein the secondary metabolites are acids and compounds regulating plant growth, removing the supernatant and re-suspending it in 0.85% concentration saline to a final cell concentration of $10^{12}$ CFU/mL;
    c) mixing each solution resulting from step b) with the teak sawdust support obtained in step a) in proportion of inoculum: support from 2:5 to 2:7; and
    d) cultivating the mixture obtained in the step c) for a period of time between 24 and 72 hours at a temperature between 25° C. and 42° C. and optionally including excipients, to obtain the biological inoculant.

2. An immobilizing process for obtaining a biological inoculant that stimulates plant growth according to claim 1, wherein the strains are Gram negative bacteria belonging to the genera *Pseudomonas*, *Burkholderia*, *Stenotrophomonas*, *Rhizobium*, *Bradyrhizobium*, *Sinorhizobium*, *Azospirillum*, *Azotobacter*, *Klebsiella*, *Enterobacter* or *Sphingomonas*.

3. An immobilizing process for obtaining a biological inoculant that stimulates plant growth according to claim 1, wherein the bacterial strain is a rhizosphere strain selected from the group consisting of at least one of strain TgLGBR285 *Stenotrophomonas* sp. and strain TgLGBR250 *Enterobacter* sp.

4. An immobilizing process for obtaining a biological inoculant that stimulates plant growth according to claim 1, wherein the temperature for growing the mixture is between 25° C. and 42° C.

5. An immobilizing process for obtaining a biological inoculant that stimulates plant growth according to claim 1, wherein the bacteria solubilize phosphorus.

6. An immobilizing process for obtaining a biological inoculant that stimulates plant growth according to claim 1, characterized in that the treated teak sawdust support has a pH between 6.8 and 7.8.

7. An immobilizing process for obtaining a biological inoculant that stimulates plant growth according to claim 1, wherein the treated teak sawdust support has a cation exchange capacity between 20 and 30 meq/100 g.

8. An immobilizing process for obtaining a biological inoculant that stimulates plant growth according to claim 1, characterized in that the treated teak sawdust support has a total count of heterotrophic, actinomycetes and fungi of less than 10 CFU/g.

9. An immobilizing process for obtaining a biological inoculant that stimulates plant growth according to claim 1, wherein the sawdust possesses a bulk density of 0.167 g/l.

10. A teak support characterized in that it is obtained according to the process in claim 1.

11. A teak support according to claim 10 wherein the teak sawdust support has a pH between 6.8 and 7.8.

12. A teak support according to claim 10 wherein the teak sawdust support has a cation exchange capacity between 20 and 30 meq/100 g.

13. A teak support according to claim 10 wherein the treated teak sawdust support has total heterotrophic counts, actinomycetes and fungi less 10 CFU/g.

14. A biological inoculant comprising a teak sawdust support that stimulates growth characterized in that it is obtained according to the process of claim 1.

15. A biological inoculant according to claim 14 characterized in that it is used to decrease a plant's time in a nursery.

16. A biological inoculant according to claim 14, wherein the biological strain is selected from the group consisting of at least one of strain TgLGBR285 *Stenotrophomonas* sp. and strain TgLGBR250 *Enterobacter* sp.

17. A biological inoculant comprising a teak sawdust support that stimulates growth characterized in that it is obtained according to the process of claim 2.

18. A biological inoculant comprising a teak sawdust support that stimulates growth characterized in that it is obtained according to the process of claim 3.

19. A biological inoculant comprising a teak sawdust support that stimulates growth characterized in that it is obtained according to the process of claim 4.

20. A biological inoculant comprising a teak sawdust support that stimulates growth characterized in that it is obtained according to the process of claim 5.

* * * * *